United States Patent
Hong et al.

(10) Patent No.: US 12,252,169 B2
(45) Date of Patent: Mar. 18, 2025

(54) MOBILE INFANT CARE DEVICE AND INFANT CARE SYSTEM INCLUDING THE SAME

(71) Applicants: Hyundai Motor Company, Seoul (KR); Kia Corporation, Seoul (KR)

(72) Inventors: Yong Pyo Hong, Seoul (KR); Hyuk Lee, Seoul (KR); Ji Hoon Oh, Uiwang-si (KR)

(73) Assignees: Hyundai Motor Company, Seoul (KR); Kia Corporation, Seoul (KR)

( * ) Notice: Subject to any disclaimer, the term of this patent is extended or adjusted under 35 U.S.C. 154(b) by 253 days.

(21) Appl. No.: 18/047,884

(22) Filed: Oct. 19, 2022

(65) Prior Publication Data

US 2023/0159076 A1 May 25, 2023

(30) Foreign Application Priority Data

Nov. 19, 2021 (KR) .......................... 10-2021-0160798

(51) Int. Cl.
*B62B 5/00* (2006.01)
*A61B 5/024* (2006.01)
(Continued)

(52) U.S. Cl.
CPC ........ *B62B 5/0076* (2013.01); *A61B 5/02438* (2013.01); *A61B 5/08* (2013.01);
(Continued)

(58) Field of Classification Search
CPC .................. A61B 5/02438; A61B 5/08; A61B 2562/0247; B62B 9/00; G05D 1/0214; G06V 20/59; G06V 40/20; G01C 21/3833
See application file for complete search history.

(56) References Cited

U.S. PATENT DOCUMENTS

2018/0325280 A1* 11/2018 Paperno ................... A47D 9/02
2021/0333391 A1* 10/2021 Lee ....................... G01S 7/4817

FOREIGN PATENT DOCUMENTS

| CN | 111353401 B * | 7/2021 | .......... B25J 11/0005 |
| KR | 101409500 B1 | 6/2014 | |

(Continued)

OTHER PUBLICATIONS

Mechanized Stroller (downloaded from The Wayback Machine) Feb. 17, 2020 from daddiorobotics.com (Year: 2020).*

(Continued)

*Primary Examiner* — Michael V Kerrigan
*Assistant Examiner* — Tanya C Sienko
(74) *Attorney, Agent, or Firm* — Slater Matsil, LLP (57) ABSTRACT

In accordance with an embodiment, a mobile infant care device includes a carrier having an inner space configured to hold an infant positioned therein, and driving wheels provided at a lower part of the carrier; a monitoring system affixed to the carrier and configured to monitor a state of the infant positioned in the inner space of the carrier; a driving system coupled to the driving wheels, the driving system configured to move a position of the carrier by driving the driving wheels; a communication system configured to wirelessly transmit a monitoring result of the monitoring system to a user terminal device or to wirelessly receive an operation input from the user terminal device; and a controller configured to cause the driving system to move the carrier based on the monitoring result of the monitoring system or the operation input received through the communication system.

20 Claims, 4 Drawing Sheets

(51) Int. Cl.
  *A61B 5/08* (2006.01)
  *B62B 9/00* (2006.01)
  *G01C 21/00* (2006.01)
  *G05D 1/00* (2024.01)
  *G06V 20/59* (2022.01)
  *G06V 40/20* (2022.01)
  *G10L 25/78* (2013.01)

(52) U.S. Cl.
  CPC ............ *B62B 9/00* (2013.01); *G05D 1/0022* (2013.01); *G05D 1/0214* (2013.01); *G06V 20/59* (2022.01); *G06V 40/20* (2022.01); *G10L 25/78* (2013.01); *A61B 2562/0247* (2013.01); *G01C 21/3833* (2020.08)

(56) References Cited

FOREIGN PATENT DOCUMENTS

| | | | | | |
|---|---|---|---|---|---|
| KR | 101652977 | B1 | * | 9/2016 | ............ G08B 21/02 |
| KR | 101970918 | B1 | * | 8/2019 | ............ A47C 31/00 |
| TW | 1722102 | B | * | 3/2021 | ............ B62B 7/00 |
| WO | WO-2018011821 | A1 | * | 1/2018 | ............ A47D 15/00 |

OTHER PUBLICATIONS

"Smart Infant-Monitoring System with Machine Learning Model to Detect Physiological Activities and Ambient Conditions" S. Shamsir et al., Conference paper May 2020 (Year: 2020).*

"Mechanized Stroller with Autonomous Robot Assisted Steering" Traczuel YouTube video Sep. 11, 2012 https://youtu.be/9e9E9nybKOY?si=MgmiAxVRrJBNZr7i (Year: 2012).*

"Design of Smart Baby Carriage Based on MCU" by Zheng Fan, etc. ISBDAI '18, Dec. 29-30, 2018, Hong Kong, Hong Kong (Year: 2018).*

Machine translation of KR 10-1970918 Jang Won, downloaded from IP.com Aug. 19, 2024 (Year: 2024).*

Machine translation of KR 10-1652977 Choi Jae Hyun, downloaded from IP.com Aug. 16, 2024 (Year: 2024).*

Machine translation of TW 1722102, Sheu, Keter et al., downloaded from IP.com Aug. 21, 2022 (Year: 2024).*

Machine translation of CN 1353401 Wu, Jichun et al., downloaded Aug. 21, 2024 (Year: 2024).*

* cited by examiner

MOBILE INFANT CARE DEVICE AND INFANT CARE SYSTEM INCLUDING THE SAME

CROSS-REFERENCE TO RELATED APPLICATIONS

This application claims the priority to and the benefit of Korean Patent Application No. 10-2021-0160798, filed on Nov. 19, 2021, in the Korean Intellectual Property Office, the disclosure of which is incorporated herein by reference.

TECHNICAL FIELD

The present invention relates to a mobile infant care device and an infant care system including the same.

BACKGROUND

Generally, when an infant is whining or anxious to sleep, their parent or guardian rocks the infant so that the infant can maintain a comfortable and stable state or sleep soundly. In the past, most infants were rocked by holding or carrying them, but recently, infants have been stably rocked to rest or sleep by using a rocking bed and thus convenience of parents has been improved.

In particular, a cradle is used to put infants to sleep, and most cradles include a cradle body having a space where an infant can lie, a support provided on the periphery of the cradle body, and four strings each having one end fixed to the upper end of the support and the other end connected to the upper periphery of the cradle body. In the cradle configured as described above, a person directly rocks the cradle body in which an infant lies in both directions to induce the infant to sleep.

However, most infants do not sleep right away while lying on the cradle body, and thus the cradle needs to be continuously rocked until the infant falls asleep. Accordingly, a person who rocks the cradle may hurt their arms and may be exhausted. In order to prevent this, there have been devised various electric cradles having a cradle body rocked by an electric motor.

However, conventional cradle bodies are fixed to a specific place, and thus there is a problem that guardians cannot deviate from fixed positions of the cradle bodies in order to care for infants.

The matters described as the background art above are only for improving the understanding of the background of the present invention and should not be taken as acknowledging that they correspond to the prior art already known to those of ordinary skill in the art.

SUMMARY

In accordance with an embodiment, a mobile infant care device includes a carrier having an inner space in which an infant is positioned and includes driving wheels provided at a lower part, a monitoring system fixed to the carrier and configured to monitor a state of the infant positioned in the inner space of the carrier, a driving system for moving a position of the carrier by driving the driving wheels, a communication system for performing wireless communication to transmit a monitoring result of the monitoring system to a user terminal device or to receive an operation input from the user terminal device, and a controller for controlling the driving system to move the carrier based on a monitoring result of the monitoring system or an operation input received through the communication system.

The monitoring system may include a camera for photographing the inner space of the carrier, and the monitoring system may monitor a motion, body temperature, or excretion of the infant based on an image captured by the camera.

The monitoring system may include a microphone for receiving a voice, and the monitoring system may monitor crying of the infant or whether the infant is sleeping based on a voice input to the microphone.

The monitoring system may include a heart rate sensor worn by the infant or a pressure sensor for sensing a pressure of the bottom of the infant, and the monitoring system may monitor a heart rate of the infant input through the heart rate sensor or respiration of the infant sensed through the pressure sensor.

The monitoring system may include an environmental sensor for sensing at least one of temperature, humidity, fine dust, and illuminance around the infant, and the monitoring system may monitor environmental data regarding a surrounding environment to which the infant is exposed, input through the environmental sensor.

The monitoring system may include a gyro sensor for sensing rotational movement, a rotational angular velocity, or a rotational acceleration of the carrier, and the monitoring system may monitor whether the carrier is overturned based on the rotational movement, rotational angular velocity, or rotational acceleration of the carrier sensed by the gyro sensor.

The controller may control the driving system to move the carrier to a preset position or a position of the user terminal device upon determining that the infant needs to be cared for based on a monitoring result detected by the monitoring system or upon reception of an operation input for requesting a call from the user terminal device.

The mobile infant care device may further include a detection sensor for sensing an obstacle adjacent to the carrier or an obstacle located on a movement path of the carrier, and the controller may determine a movement path for moving the carrier to a preset position or the position of the user terminal device based on detection information of the detection sensor, and control the driving system based on the determined movement path.

The mobile infant care device may further include a mapping system for performing mapping to create a map based on detection information of the detection sensor, and the controller may determine a movement path of the carrier based on a mapping result of the mapping system and the detection information of the detection sensor.

The mobile infant care device may further include a speaker for generating a warning sound based on a monitoring result of the monitoring system or providing a pre-stored sound or an input sound based on an operation input received through the communication system.

The mobile infant care device may further include an actuator for generating rocking in the inner space of the carrier with respect to the lower part provided with the driving wheels during operation, and the controller may control operation of the actuator based on a monitoring result of the monitoring system or an operation input received through the communication system.

In accordance with another embodiment of the present invention, an infant care system includes the mobile infant care device, including a user terminal device for wirelessly communicating with the communication system to receive a monitoring result of the monitoring system or to transmit an operation input received from a user, and a server for receiving a monitoring result of the monitoring system from the communication system or the user terminal device, storing the monitoring result in a database, and transmitting analysis data obtained by comparing the received monitoring result with data pre-stored in the database to the user terminal device.

The server may receive body data of an infant input by the user using the user terminal device, and transmit care data regarding care of the infant to the user terminal device based on the received body data and monitoring results.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF ILLUSTRATIVE EMBODIMENTS

Specific structural and functional descriptions of embodiments of the present invention disclosed in the present specification or application are illustrated for the purpose of describing embodiments according to the present invention, and embodiments according to the present invention may be implemented in various forms and should not be construed as being limited to the embodiments described in the present specification and application.

While embodiments according to the present invention are susceptible to various modifications and alternative forms, specific embodiments are shown by way of example in the drawings. However, the present invention should not be construed as being limited to the embodiments set forth herein, but on the contrary, the present invention is to cover all modifications, equivalents, and alternatives falling within the spirit and scope of the present invention.

The terms "first" and/or "second" are used to describe various components, but such components are not limited by these terms. The terms are used to discriminate one component from another component. For example, a first component may be called a second component and the second component may be called the first component within the technical spirit of the present invention.

When a component is "coupled" or "connected" to another component, it should be understood that a third component may be present between the two components although the component may be directly coupled or connected to the other component. When a component is "directly coupled" or "directly connected" to another component, it should be understood that no element is present between the two components. Further, other representations describing a relationship between components, that is, "between", "immediately between", "adjacent to" and "directly adjacent to" should be construed likewise.

The terms used in the specification of the present invention are merely used in order to describe particular embodiments, and are not intended to limit the scope of the present invention. An element described in the singular form is intended to include a plurality of elements unless the context clearly indicates otherwise. In the specification of the present invention, it will be further understood that the term "comprise" or "include" specifies the presence of a stated feature, figure, step, operation, component, part or combination thereof, but does not preclude the presence or addition of one or more other features, figures, steps, operations, components, or combinations thereof.

All the terms that are technical, scientific or otherwise agree with the meanings as understood by a person skilled in the art unless defined to the contrary. Common terms as found in dictionaries should be interpreted in the context of the related technical writings not too ideally or impractically unless expressly disclosed herein.

Hereinafter, the present invention will be described in detail by describing preferred embodiments of the present invention with reference to the accompanying drawings. Like reference numerals in each figure indicate like elements.

Embodiments of the present invention relates to a mobile infant care device for generating shaking in a carrier provided with a space where an infant lies or moves by itself, and intelligently caring for infants, and an infant care system including the same.

Figure 1:
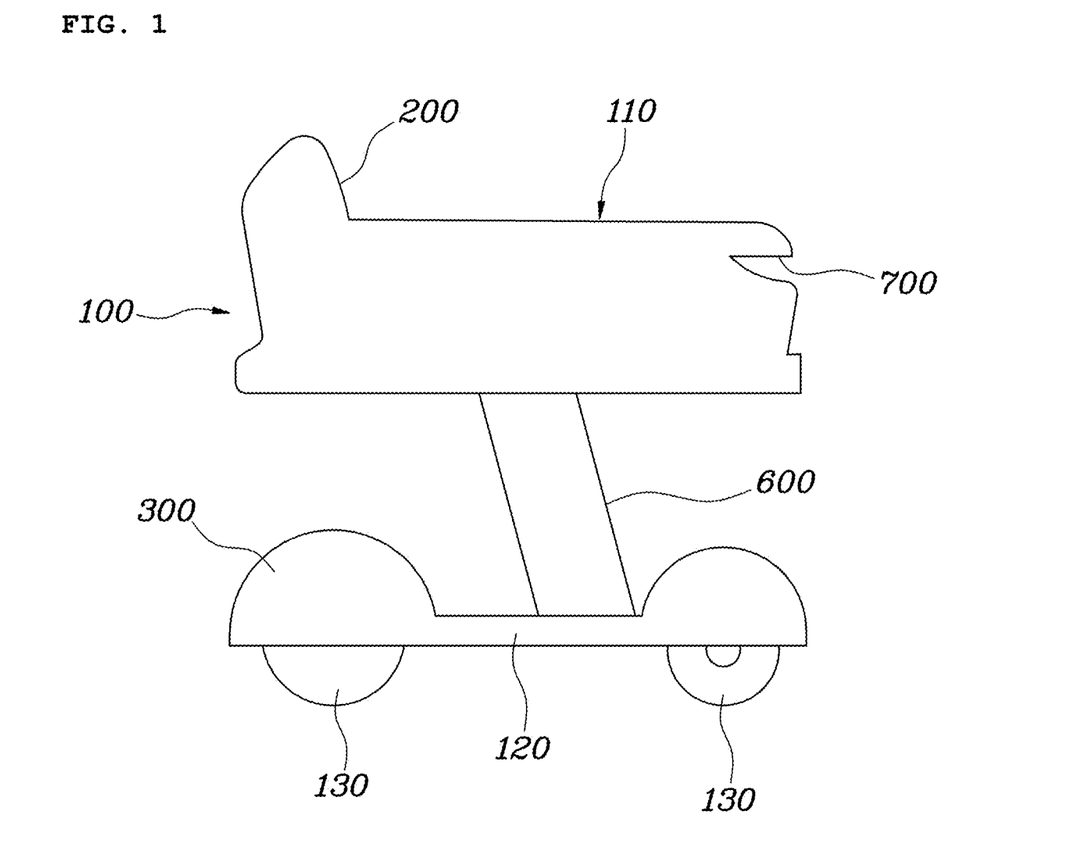
FIG. 1 is a side view of a mobile infant care device according to an embodiment of the present invention.
Figure 2:
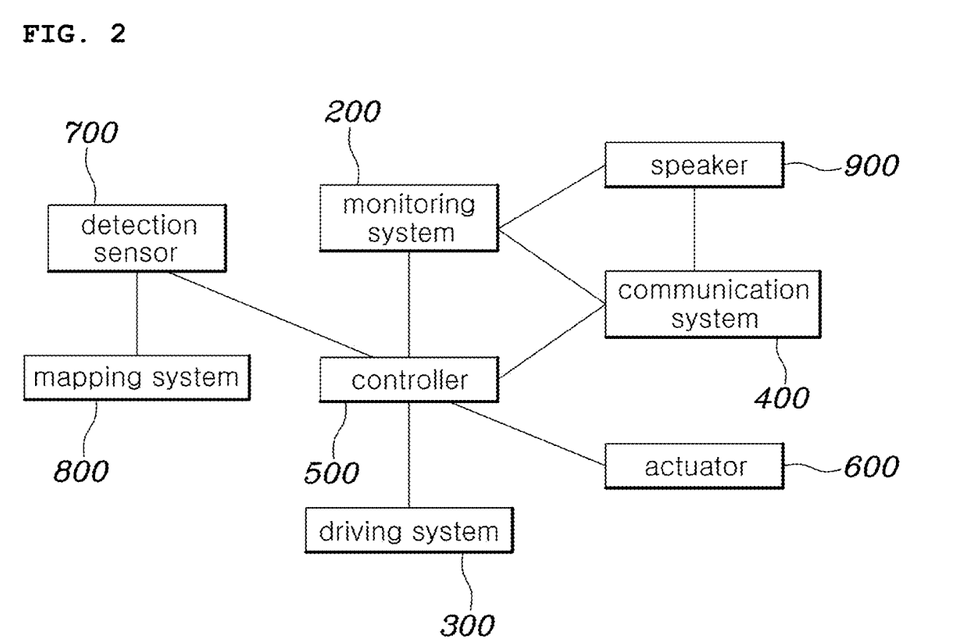
FIG. 2 is a block diagram of the mobile infant care device according to an embodiment of the present invention.

FIG. 1 is a side view of a mobile infant care device according to an embodiment of the present invention, and FIG. 2 is a block diagram of the mobile infant care apparatus according to an embodiment of the present invention.

Figure 4:
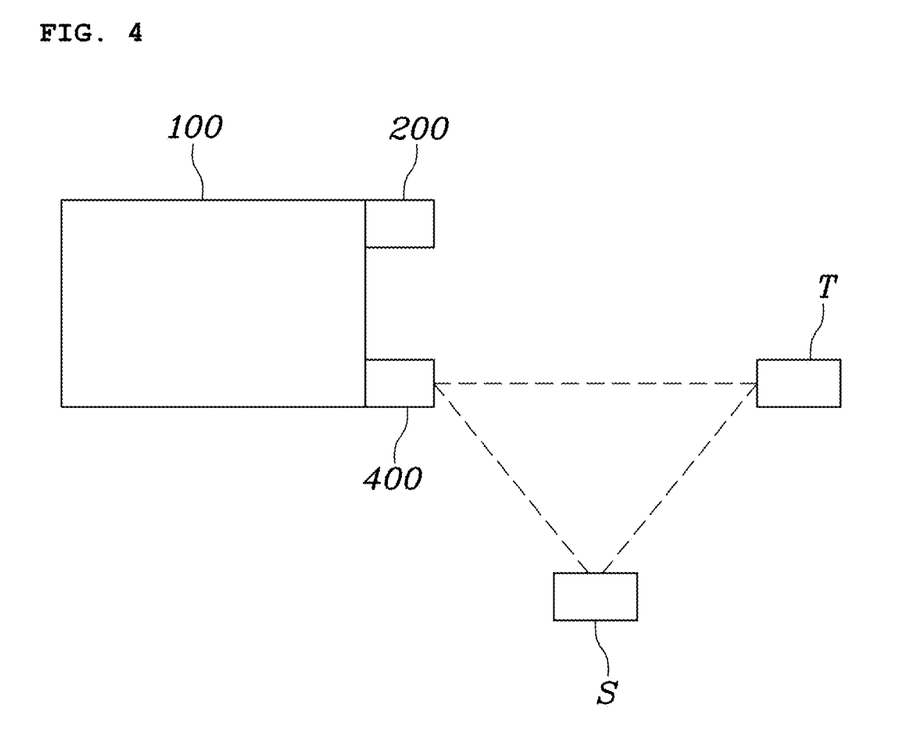
FIG. 4 is a block diagram of an infant care system including the mobile infant care device according to an embodiment of the present invention.

Referring to FIGS. 1, 2 and 4, the mobile infant care device according to an embodiment of the present invention includes a carrier 100 having an inner space 110 in which an infant is located and including driving wheels 130 provided at the lower part 120, a monitoring system 200 fixed to the carrier 100 and configured to monitor the state of the infant located in the inner space 110 of the carrier 100, a driving system 300 for moving the position of the carrier 100 by driving the driving wheels 130, a communication system 400 for performing wireless communication to transmit a monitoring result of the monitoring system 200 to a user terminal device T or to receive an operation input from the user terminal device T, and a controller 500 for controlling the driving system 300 to move the carrier 100 based on a monitoring result of the monitoring system 200 or an operation input received through the communication system 400.

Specifically, the carrier 100 may have various shapes, but may be hardware in the shape of a general stroller. In particular, the carrier 100 has the bed-shaped inner space 110 in which an infant can lie, and the lower part 120 supporting the inner space 110 includes the driving wheels 130 for allowing the carrier 100 to be movable. Although the driving wheels 130 may be driven by the driving system 300, they may also be rotatable by external force of the user.

The monitoring system 200 is a component fixed to the carrier 100, and in one embodiment, the monitoring system 200 may be positioned in the inner space 110 of the carrier 100 or positioned above the inner space 110 to monitor the infant from above.

The monitoring system 200 may receive sensing data from various sensors which will be described later and monitor the state of the infant by combining the received sensing data.

The operation of the driving system 300 is controlled by the controller 500, and the driving system 300 can generate a driving force for driving the driving wheels 130. In one embodiment, the driving system 300 may be a motor that receives power to generate a driving force and may include a battery for storing charged power.

The communication system 400 is a wireless communication device and may be a device that performs wireless data communication with a short-distance or long-distance terminal or performs data communication with a server S as will be described below. In particular, the communication system 400 may transmit a monitoring result of the monitoring system 200 received from the monitoring system 200 to the user terminal device T and may receive an operation input from the user terminal device T and transmit the same to the controller 500.

A communication network used by the communication system 400 includes both wired and wireless communication networks. For example, a wired/wireless Internet network may be used as a communication network. Here, wired networks include the Internet, a cable network, and a public telephone network (PSTN), and wireless communication networks include CDMA, WCDMA, GSM, Evolved Packet Core (EPC), Long Term Evolution (LTE), WiBro, and the like. The present invention is not limited thereto and may be used, for example, in a cloud computing network under a cloud computing environment, a 5G network, and the like.

If the communication network is a wired communication network, an access point within the communication network can access a switching center of a telephone company. In the case of a wireless communication network, data can be processed by accessing an SGSN or Gateway GPRS Support Node (GGSN) operated by a communication company or data can be processed by accessing various repeaters such as a base transceiver station (BTS), NodeB, and e-NodeB.

In addition, the communication network may include an access point (AP). Here, the access point includes a small base station, such as a femto or pico base station, which is installed in a building. Of course, the access point may include a short-range communication module for performing short-range communication such as Zigbee and Wi-Fi. The access point may use TCP/IP or real-time streaming protocol (RTSP) for wireless communication. Here, short-range communication may be performed using various standards such as Bluetooth, Zigbee, infrared, radio frequency (RF) such as ultra-high frequency (UHF) and very high frequency (VHF), and ultra-wideband communication (UWB) in addition to Wi-Fi. Accordingly, the access point may detect the location of a data packet, designate a best communication path for the detected location, and deliver the data packet to the user terminal device T or server S along the designated communication path. The access point may share multiple lines in a general network environment and includes, for example, a router and a repeater.

The monitoring system 200, the communication system 400, and the controller 500 according to an exemplary embodiment of the present invention may be implemented by a nonvolatile memory (not shown) that store an algorithm configured to control operations of various components of a vehicle or data related to software commands for executing the algorithm, and a processor (not shown) configured to perform operations which will be described below using data stored in the memory. Here, the memory and the processor may be implemented as separate chips. Alternatively, the memory and the processor may be implemented as a single integrated chip. The processor may take the form of one or more processors.

Although specific positions of the communication system 400 and the controller 500 are not indicated, they may be components fixed to the carrier 100. The communication system 400 and the controller 500 may be connected to transmit/receive signals or data to/from the monitoring system 200 and the driving system 300 and may be located in any part of the carrier 100.

The controller 500 may move the carrier 100 based on the state of the infant according to a monitoring result of the monitoring system 200 or may move the carrier 100 based on an operation input of the user terminal device T input to the communication system 400.

More specifically, upon determining that the infant needs to be cared for based on a monitoring result sensed by the monitoring system 200 or upon reception of an operation input for requesting a call from the user terminal device T, the controller 500 may control the driving system 300 such that the carrier 100 moves to a preset position or the position of the user terminal device T.

In one embodiment, the controller 500 may control the driving system 300 to move the carrier 100 along a movement path to a preset position or the position of the user terminal device T.

Here, the preset position may be a single position or a plurality of positions designated by the user, for example, designated positions inside a building, such as a living room, a kitchen, and a main room. The controller 500 may set a movement path along which the carrier 100 moves to a preset position or the position of the user terminal device T and may control the driving system 300 according to the set movement path.

In addition, when there is a plurality of preset positions, the controller 500 may receive a user's selection through the terminal device T and set a movement path according to the user's selection or may select one of the plurality of preset positions based on a monitored state of the infant and set a movement path according to the selected result.

Alternatively, the controller 500 may receive an operation input for selecting any one of a preset position and the position of the user terminal device T from the terminal device T and set a movement path according to or monitor a movement path according to the user's selection, or select any one of a preset position and the position of the user terminal device T based on the monitored state of the infant and set a movement path according to the selected result.

For example, upon determining that diaper change is necessary for the infant as a result of monitoring of the monitoring system 200, the controller 500 may set a movement path to a toilet among preset positions. In addition, upon determining that the infant's body temperature is high as a result of monitoring of the monitoring system 200, the controller 500 may set a movement path to the position of the user terminal device T instead of a preset position.

More specifically, the controller 500 may turn on/off a function of automatically moving the carrier 100 to a preset position or the position of the user terminal device T based on a monitoring result sensed by the monitoring system 200. When the automatic mode is off, the controller 500 may control the driving system 300 to move the carrier 100 to a preset position or to the position of the user terminal device T only when an operation input for requesting a call is received from the user terminal device T.

In addition, upon determining that the infant needs to be cared for as a result of monitoring of the monitoring system 200, the communication system 400 may transmit a signal to activate a voice listening function in the user terminal device T. In this case, a position at which a movement path along which the driving system 300 will move the carrier 100 is set may be input to the user terminal device T.

Figure 3:
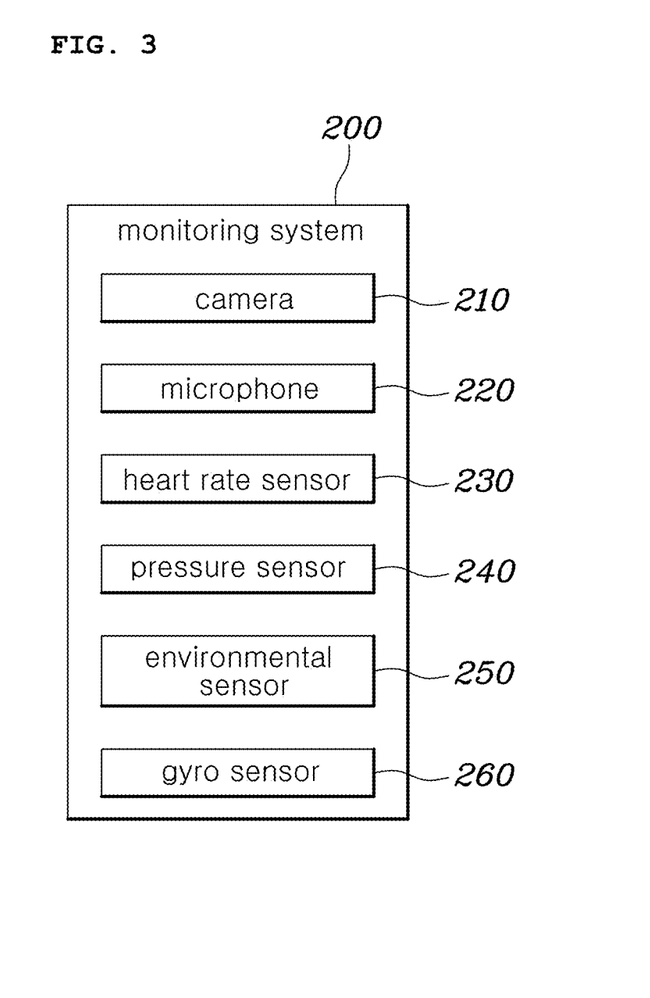
FIG. 3 is a block diagram showing a monitoring system according to an embodiment of the present invention.

FIG. 3 is a block diagram illustrating the monitoring system 200 according to an embodiment of the present invention.

Referring to FIG. 3, the monitoring system 200 includes a camera 210 for photographing the inner space 110 of the carrier 100, and the monitoring system 200 can monitor the motion, body temperature, or excretion of the infant based on images captured by the camera 210.

The camera 210 includes a general closed circuit television (CCTV) camera 210 or an Internet protocol (IP) camera 210 as a surveillance camera 210. In addition, the camera 210 may include a pan-tilt-zoom (PTZ) camera 210 capable of panning, tilting, and zooming operations as well as a fixed camera 210.

The camera 210 may monitor the motion of the infant while continuously photographing the infant. In particular, the camera 210 may monitor the presence or absence of the infant, movement or whether the infant is sleeping through a captured image.

In addition, the camera 210 may include an infrared camera 210 for sensing the temperature in a captured image. Accordingly, the camera 210 may monitor whether the infant is excreted by sensing the infant's body temperature or sensing the temperature around the infant's diaper. In addition, the monitoring system 200 may further include a temperature sensor for sensing the body temperature of the infant.

In addition, the camera 210 may sense the illuminance around the infant based on a captured image instead of an illuminance sensor which will be described later. In addition, the camera 210 may capture an image or a photo according to operation input of the user's terminal and may transmit a captured image or photo of the infant to the user's terminal device T or the server S through the communication system 400.

The monitoring system 200 may include a microphone 220 for receiving voice input, and thus the monitoring system 200 can monitor crying of the infant or monitor whether the infant is sleeping based on voice input applied to the microphone 220.

The microphone 220 is a device for receiving a voice and may detect crying of the infant or sound according to sleeping of the infant.

In addition, the monitoring system 200 includes a heart rate sensor 230 worn on the infant or a pressure sensor 240 for sensing the pressure of the bottom of the infant, and thus the monitoring system 200 can monitor the heart rate of the infant input through the heart rate sensor 230 and monitor the respiration of the infant sensed through the pressure sensor 240.

The heart rate sensor 230 may be selectively worn on the infant, and in particular, may be worn to be attached to a wrist or ankle of the infant. The heart rate sensor 230 may sense the heartbeat of the infant.

The pressure sensor 240 is located on the bottom of the inner space 110 in which the infant is positioned, and in particular, may be located under the infant. The pressure sensor 240 may sense the surface pressure acting on the bottom surface of the inner space 110 of the carrier 100 and sense the respiration cycle of the infant through change in pressure distribution according to periodic respiration of the infant.

The monitoring system 200 may include an environmental sensor 250 for sensing at least one of temperature, humidity, fine dust, and illuminance around the infant, and thus the monitoring system 200 can monitor environmental data of an environment to which the infant is exposed, input through the environmental sensor 250.

Here, the environmental sensor 250 is a temperature sensor for sensing the ambient air temperature, a humidity sensor for sensing the humidity of the air, a dust sensor for sensing the concentration of fine dust, or an illuminance sensor for sensing the ambient illuminance to which the carrier 100 is exposed, or a combination thereof.

In particular, the environmental data refers to data regarding the environment to which the infant is exposed and may refer to data related to the health of the infant or data related to deep sleep of the infant.

In addition, the monitoring system 200 may determine whether the environment is suitable for the infant to be exposed to based on the monitored environment data and may transmit a determination result to the user terminal device T or the server S.

The monitoring system 200 includes a gyro sensor 260 for sensing rotational movement, rotational angular velocity or rotational acceleration of the carrier 100, and thus the monitoring system 200 can monitor whether the carrier 100 is overturned based on the rotational movement, rotational angular velocity, or rotational acceleration of the carrier 100, sensed by the gyro sensor 260.

The gyro sensor 260 in the form of a chip in which a gyroscope is applied with MEMS technology may sense a rotational angular velocity. Further, the gyro sensor 260 may sense rotational movement or rotational acceleration through integration or differentiation of an angular velocity. The monitoring system 200 may detect whether the carrier 100 is overturned through the rotational movement, rotational angular velocity, or rotational acceleration of the carrier 100 sensed by the gyro sensor 260.

In another embodiment, the monitoring system 200 may monitor a roll, a pitch, etc. of the carrier 100 by including an acceleration sensor.

A detection sensor 700 for detecting an obstacle adjacent to the carrier 100 or an obstacle located on a movement path of the carrier 100 may be further included, and the controller 500 may determine a movement path along which the carrier 100 will be moved to a preset position or the position of the user terminal device T based on detection information of the detection sensor 700, and control the driving system 300 based on the determined movement path.

The detection sensor 700 may be mounted on the carrier 100 in a state in which it is disposed toward the outside of the carrier 100 and may detect an obstacle adjacent to the carrier 100 or an obstacle located on a set movement path of the carrier 100. For example, the detection sensor 700 may be a radar sensor, a lidar sensor, an ultrasonic sensor, or a camera sensor (image sensor).

In one embodiment, the detection sensor 700 includes a radar sensor, a lidar sensor, an ultrasonic sensor, or a camera sensor (image sensor), and the controller 500 may determine a movement path along which the carrier 100 will be moved to a preset position or the position of the user terminal device T and control the driving system 300 based on the determined movement path.

In particular, when the detection sensor 700 detects that an obstacle is present on the movement path of the carrier 100, the controller 500 may correct the movement path to avoid the obstacle, and when it is impossible to avoid the obstacle, may transmit warning information to the user terminal device T through the communication system 400.

In another embodiment, a mapping system 800 for performing mapping through simultaneous localization and mapping (SLAM) based on detection information of the detection sensor 700 may be further included, and the controller 500 may determine a movement path of the carrier 100 based on a mapping result of the mapping system 800 and detection information of the detection sensor 700.

Specifically, the mapping system 800 may perform mapping to create a map of the external environment while detecting the position of the carrier 100 based on a simultaneous localization and mapping (SLAM) algorithm. In particular, the carrier 100 may include a position detection sensor for detecting the position of the carrier 100, such as a GPS sensor or a gyro sensor. It is known that, in the process of implementing the SLAM algorithm, additional sensor information of the detection sensors 700 (an infrared sensor, a radar sensor, a lidar sensor, an ultrasonic sensor, or the like) may be used.

When the controller 500 moves the carrier 100 based on a monitoring result of the monitoring system 200 or an operation input received through the communication system 400, the controller 500 may move the carrier 100 along a movement path based on a map mapped by the mapping system 800.

A speaker 900 that generates a warning sound based on a monitoring result of the monitoring system 200 or provides a pre-stored or input sound based on an operation input received through the communication system 400 may be further included.

The speaker 900 may generate a warning sound upon determining that the infant needs to be cared for as a result of monitoring of the monitoring system 200. In particular, the speaker 900 may generate a warning sound upon determining that urgent care is needed due to a problem in respiration or the heartbeat of the infant, for example, as a monitoring result.

In addition, the speaker 900 may provide a pre-stored or input sound based on an operation input received through the communication system 400. Here, the pre-stored or input sound may be music that helps the infant sleep well, such as a lullaby or classical music. The pre-stored sound may be a user's voice pre-stored through the microphone 220 or the user terminal device T through recording, and the input sound may be received from the server S or the user terminal device T.

An actuator 600 for generating rocking in the inner space 110 of the carrier 100 with respect to the lower part 120 provided with the driving wheels 130 during operation may be further included, and the controller may control the operation of the actuator 600 based on a monitoring result of the monitoring system 200 or an operation input received through the communication system 400.

The actuator 600 may be operated by an electric motor or through a solenoid method. When the actuator 600 operates, rotation of the driving wheels 130 is fixed and thus the inner space 110 positioned at the upper part of the carrier 100 with respect to the lower part 120 fixed to the floor may rock. Rocking may be a rotational motion based on a central axis.

In another embodiment, the controller 500 may generate rocking vibration in the carrier 100 by alternately driving the driving wheels 130 in the forward direction and the reverse direction.

FIG. 4 is a block diagram of an infant care system including the mobile infant care device according to an embodiment of the present invention.

Referring to FIG. 4, the infant care system according to an embodiment of the present invention is an infant care system including the mobile infant care device, and includes a user terminal device T that wirelessly communicates with the communication system 400 to receive a result monitored by the monitoring system 200 or to transmit an operation input received from a user, and a server S that receives the monitoring result of the monitoring system 200 from the communication system 400 or the user terminal device T, stores the received monitoring result in a database, and transmits analysis data obtained by comparing the received monitoring result with data pre-stored in the database to the user terminal device T.

The user terminal device T may transmit/receive data to/from the communication system 400 of the infant care device through wireless communication, and in particular, receive a monitoring result of the monitoring system 200 from the communication system 400 or transmit an operation input received from the user to the communication system 400.

The user terminal device T may be a communication device such as a mobile phone or a smartphone, or a portable device such as a tablet computer.

The server S may be hardware or software in which a database DB for storing data is constructed and may be capable of wireless communication with the communication system 400 and the user terminal device T. Monitoring results of the monitoring system 200 transmitted from the communication system 400 may be continuously stored in the database of the server S. In addition, average monitoring data of infants may be transmitted to the database of the server S through the Internet.

In addition, the server S may compare a monitoring result of the monitoring system 200 received through the communication system 400 with data pre-stored in the database to analyze the monitoring result. In one embodiment, the server S may derive graphs of a sleep pattern and health pattern of an infant, an environmental pattern to which an infant is exposed, and the like based on the monitoring results, and compare the graphs with data stored in the database to determine characteristics of the infant.

In addition, the server S may receive body data of the infant input by the user using the user terminal device T, and transmit care data regarding care of the infant to the user terminal device T based on the received body data and monitoring results.

The body data may be data that can be input from the user, such as a growth period from the birth date of the infant, height, weight, and sex.

In addition, the server S may transmit care data that can help in caring for the infant to the user terminal device T based on the received body data and monitoring results. For example, the server S may provide massage tips helpful to the infant based on the growth period of the infant or provide tips on maintaining humidity when the environment to which the infant is exposed is dry as a result of monitoring.

According to the mobile infant care device and the infant care system including the same of the present invention, it is possible to continuously monitor the state of an infant on behalf of a guardian, thereby safely securing free time from childcare for the guardian.

In addition, it is possible to reduce the labor of the guardian by moving the infant to the guardian and putting the infant to sleep in place of the guardian when the infant needs to be cared for or when the guardian requests it.

In accordance with some embodiments of the present invention a mobile infant care device and an infant care system may continuously monitor infants and move them to guardians when they need care.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A mobile infant care device comprising:
   a carrier having an inner space configured to hold an infant positioned therein, and driving wheels provided at a lower part of the carrier to produce a monitoring result;
   a monitoring system affixed to the carrier and configured to monitor a state of the infant positioned in the inner space of the carrier;
   a driving system coupled to the driving wheels, the driving system configured to move a position of the carrier by driving the driving wheels;
   a communication system configured to wirelessly transmit the monitoring result of the monitoring system to a user terminal device or to wirelessly receive an operation input from the user terminal device; and
   a controller configured to:
      cause the driving system to move the carrier based on the monitoring result of the monitoring system or the operation input received through the communication system, and
      cause the driving system to move the carrier to a preset position based on the monitoring result of the monitoring system or a preset position of a position of the user terminal device upon reception of an operation input for requesting a call from the user terminal device.

2. The mobile infant care device of claim 1, wherein the monitoring system includes a camera configured to capture a visual image of the inner space of the carrier, wherein the monitoring system is configured to monitor a motion, body temperature, or excretion of the infant based on the visual image captured by the camera.

3. The mobile infant care device of claim 1, wherein the monitoring system includes a microphone configured to capture sound made by the infant, and the monitoring system is further configured to determine whether the infant is crying or sleeping based on the captured sound.

4. The mobile infant care device of claim 1, wherein the monitoring system includes a heart rate sensor configured to be worn by the infant or a pressure sensor configured to sense a pressure of a bottom of the infant,
   wherein the monitoring system is configured to monitor a heart rate of the infant input via the heart rate sensor or a respiration of the infant sensed via the pressure sensor.

5. The mobile infant care device of claim 1, wherein the monitoring system includes an environmental sensor configured to sense at least one of a temperature, humidity, fine dust, and illuminance around the infant,
   wherein the monitoring system is configured to monitor environmental data regarding a surrounding environment to which the infant is exposed, input through the environmental sensor.

6. The mobile infant care device of claim 1, wherein the monitoring system includes a gyro sensor configured to sense a rotational movement, a rotational angular velocity, or a rotational acceleration of the carrier,
   wherein the monitoring system is configured to determine whether the carrier is overturned based on the rotational movement, rotational angular velocity, or rotational acceleration of the carrier sensed by the gyro sensor.

7. The mobile infant care device of claim 1, further comprising a detection sensor configured to sense an obstacle adjacent to the carrier or an obstacle located on a movement path of the carrier,
   wherein the controller is configured to determine an updated movement path for moving the carrier to a preset position or a position of the user terminal device based on detection information of the detection sensor, and is configured to control the driving system based on the determined movement path.

8. The mobile infant care device of claim 7, further comprising a mapping system configured to create a map based on the detection information of the detection sensor,
   wherein the controller is configured to determine a movement path of the carrier based on a mapping result of the mapping system and the detection information of the detection sensor.

9. The mobile infant care device of claim 1, further comprising a speaker configured to generate a warning sound based on the monitoring result of the monitoring system or configured to provide a pre-stored sound or an input sound based on the operation input received through the communication system.

10. The mobile infant care device of claim 1, further comprising an actuator configured to cause rocking in the inner space of the carrier with respect to the lower part provided with the driving wheels during operation,
    wherein the controller is configured to control operation of the actuator based on the monitoring result of the monitoring system or the operation input received through the communication system.

11. An infant care system comprising:
    a carrier having an inner space configured to hold an infant positioned therein, and driving wheels provided at a lower part of the carrier;
    a monitoring system affixed to the carrier and configured to monitor a state of the infant positioned in the inner space of the carrier;
    a driving system coupled to the driving wheels, the driving system configured to move a position of the carrier by driving the driving wheels;
    a communication system configured to wirelessly transmit a monitoring result of the monitoring system to a user terminal device or to wirelessly receive an operation input from the user terminal device;
    a controller configured to cause the driving system to move the carrier based on the monitoring result of the monitoring system or the operation input received through the communication system;
    the user terminal device configured to wirelessly communicate with the communication system and configured to receive the monitoring result of the monitoring system or to transmit the operation input based on input to the user terminal device; and
    a server configured to receive the monitoring result of the monitoring system from the communication system or the user terminal device, store the monitoring result in a database, and transmit analysis data obtained by comparing the received monitoring result with data pre-stored in the database to the user terminal device, wherein the controller is configured to cause the driving system to move the carrier to a preset position based on the monitoring result of the monitoring system or a preset position of a position of the user terminal device upon reception of an operation input for requesting a call from the user terminal device.

12. The infant care system of claim 11, wherein the server is configured to receive body data of an infant input by a user using the user terminal device, and transmit care data regarding care of the infant to the user terminal device based on the received body data and the monitoring result.

13. The infant care system of claim 11, wherein the monitoring system includes a microphone configured to capture sound made by the infant, and the monitoring system is further configured to determine whether the infant is crying or sleeping based on the captured sound.

14. The infant care system of claim 11, wherein the monitoring system includes a heart rate sensor configured to be worn by the infant or a pressure sensor configured to sense a pressure of a bottom of the infant,
wherein the monitoring system is configured to monitor a heart rate of the infant input via the heart rate sensor or a respiration of the infant sensed via the pressure sensor.

15. The infant care system of claim 11, wherein the monitoring system includes an environmental sensor configured to sense at least one of a temperature, humidity, fine dust, and illuminance around the infant,
wherein the monitoring system is configured to monitor environmental data regarding a surrounding environment to which the infant is exposed, input through the environmental sensor.

16. A method of operating a mobile infant care device having a carrier comprising an inner space in which an infant is positioned, the method comprising:
monitoring a state of the infant by a monitoring system affixed to the carrier and positioned in the inner space of the carrier to provide a monitoring result;
wirelessly communicating the monitoring results to a user terminal device or wirelessly receiving an operation input from the user terminal device;
moving a position of the carrier by a driving system coupled to driving wheels provided at a lower part of the carrier in response to the monitoring result or the operation input; and
controlling the driving system to move the carrier to a preset position based on the monitoring result of the monitoring system or a preset position of a position of the user terminal device upon reception of an operation input for requesting a call from the user terminal device.

17. The method of claim 16, further comprising:
capturing, by a microphone, a sound made by the infant; and
determining whether the infant is crying or sleeping based on the captured sound.

18. The method of claim 16, further comprising:
sensing, using a gyro sensor, a rotational movement, a rotational angular velocity, or a rotational acceleration of the carrier; and
determining whether the carrier is overturned based on the sensed rotational movement, the sensed rotational angular velocity, or the sensed rotational acceleration.

19. The method of claim 16, further comprising:
sensing, by a detection sensor, an obstacle adjacent to the carrier or an obstacle located on a movement path of the carrier; and
correcting the movement path to avoid the sensed obstacle.

20. The method of claim 16, further comprising rocking the inner space of the carrier using an actuator.

* * * * *